United States Patent [19]

Kleiner

[11] Patent Number: 5,698,729
[45] Date of Patent: Dec. 16, 1997

[54] PROCESS FOR PREPARING 6-ALKOXY-(6H)-DIBENZO[C,E][1,2]-OXAPHOSPHORINES

[75] Inventor: Hans-Jerg Kleiner, Kronberg, Germany

[73] Assignee: Hoechst Aktiengesellschaft, Frankfurt, Germany

[21] Appl. No.: 792,284

[22] Filed: Jan. 31, 1997

[30] Foreign Application Priority Data

Feb. 1, 1996 [DE] Germany .................. 196 03 570.8

[51] Int. Cl.⁶ .................................................. C07F 9/6574
[52] U.S. Cl. ............................................................. 558/82
[58] Field of Search ................................................ 558/82

[56] References Cited

U.S. PATENT DOCUMENTS

| | | |
|---|---|---|
| 4,185,006 | 1/1980 | Rasberger et al. .......... 260/458 |
| 5,008,426 | 4/1991 | Kleiner et al. . |
| 5,064,885 | 11/1991 | Müller et al. . |
| 5,096,935 | 3/1992 | Kleiner et al. . |

FOREIGN PATENT DOCUMENTS

| | | |
|---|---|---|
| 0292786 | 8/1992 | European Pat. Off. . |
| 0304782 | 12/1993 | European Pat. Off. . |
| 29 26 897 | 1/1980 | Germany . |
| 53-56250 | 5/1978 | Japan . |
| 853982 | of 0000 | United Kingdom . |

OTHER PUBLICATIONS

E. A. Chernyshev,"Organophosphorus Heterocyclic Compounds III, Synthesis and Reactions of 6–Chloro–6H–Dibenz(c,e) (1,2) Oxaphosphorine", Journal of General Chemistry USSR, vol. 42, No. 1, part 1, Jan. 1972.

B. M. Gladshtein and L. N. Shitov, "Synthesis of Alkylphosphonous Esters", Journal of General Chemistry USSR, pp. 1913–1915 (1969).

Chernyshev, E. A., et al, Zh. Obshch Khim 43:93–98 (1972).

Primary Examiner—Michael G. Ambrose
Attorney, Agent, or Firm—Connolly and Hutz

[57] ABSTRACT

The invention relates to a process for preparing 6-alkoxy-(6H)-dibenzo[c,e][1,2]-oxaphosphorines of the formula (I)

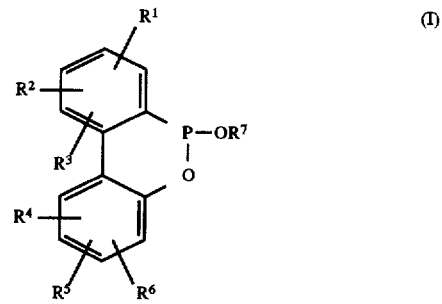

where $R^1$ to $R^6$ independently of one another are halogen, $(C_1-C_6)$alkyl or $(C_1-C_6)$alkoxy and $R^7$ is $(C_1-C_8)$alkyl, which comprises adding 6-halo-(6H)-dibenzo[c,e][1,2]-oxaphosphorines of the formula (II)

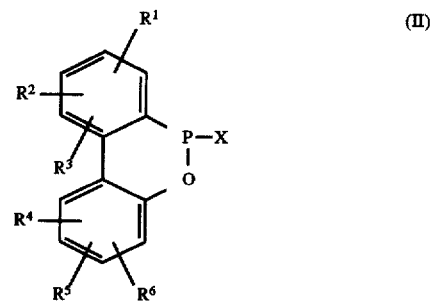

where $R^1$ to $R^6$ have the meaning specified above and X is halogen, to alcohols $R^7OH$, where $R^7$ has the meaning given above, at temperatures of −30° to +5° C. and then introducing ammonia at this temperature.

15 Claims, No Drawings

PROCESS FOR PREPARING 6-ALKOXY-(6H)-DIBENZO[C,E][1,2]-OXAPHOSPHORINES

DESCRIPTION

The invention relates to a process for preparing 6-alkoxy-(6H)-dibenzo[c,e][1,2]-oxaphosphorines.

6-Alkoxy-(6H)-dibenzo[c,e][1,2]-oxaphosphorines are valuable additives for increasing the thermal stability of aliphatic polycarbonates (EP-B 0 292 786). Addition during the preparation of polyesters decreases their tendency to discoloration and increases the resistance to hydrolysis (Japan. Kokai 7856250). They are further valuable intermediates for preparing photoinitiators (EP-A 0 304 782).

They have been prepared to date by reacting 6-chloro-(6H)-dibenzo[c,e][1,2]-oxaphosphorine with alcohols in the presence of tertiary bases such as pyridine using suitable solvents (E. A. Chernyshev et al., Zh. Obshch Khim. 42, 93 (1972)). A yield of only 54% of theory is described for this process.

There was therefore the need to develop a process for preparing 6-alkoxy-(6H)-dibenzo[c,e][1,2]-oxaphosphorines, which gives the desired products in high yield and purity without requiring great amounts of technical resources.

This object is achieved by a process for preparing 6-alkoxy-(6H)-dibenzo[c,e][1,2]-oxaphosphorines of the formula (I)

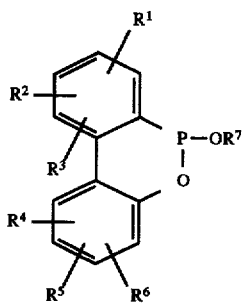

where $R^1$ to $R^6$ independently of one another are halogen, $(C_1-C_6)$alkyl or $(C_1-C_6)$alkoxy and $R^7$ is $(C_1-C_8)$alkyl, which comprises adding 6-halo-(6H)-dibenzo[c,e][1,2]-oxaphosphorines of the formula (II)

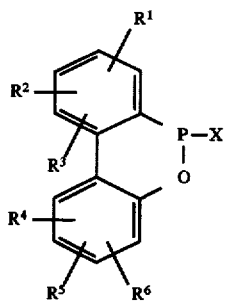

where $R^1$ to $R^6$ have the meaning specified above and X is halogen, to alcohols $R^7OH$, where $R^7$ has the meaning given above, at temperatures of $-30°$ to $+5°$ C. and then introducing ammonia at this temperature.

The process is of importance, e.g., for preparing compounds of the formula (I) where one, in particular two, of each of the radicals $R^1$ to $R^3$ and $R^4$ to $R^6$ are hydrogen and $R^7$ is $(C_1-C_4)$alkyl. The reaction is also of great importance for the unsubstituted compounds having $R^1$ to $R^6$ equal to hydrogen.

Suitable alcohols $R^7OH$ are, e.g., methanol, ethanol, isopropanol, butanol or octanol. Ethanol, in particular, is preferred. The alcohols should be as free as possible from water. In many cases it has proved to be useful to use alcohols in excess; in this case, in particular, an excess of chlorooxaphosphorines: alcohol of 1:1.1 to 1:20, preferably 1:1.1 to 1:1.15 mol has proved to be expedient.

In addition, the use of inert solvents, such as toluene or cyclohexane, is expedient.

The process is advantageously carried out in such a manner that the chlorooxaphosphorine is added to the alcohol, if appropriate mixed with the solvent, under a nitrogen atmosphere at $-30°$ C. to $0°$ C., in particular $-20°$ to $-10°$ C., and the hydrogen halide formed is then reacted with ammonia.

Good results are achieved, e.g., if the chlorooxaphosphorine addition lasts for about one to two hours and the reaction with the ammonia is likewise completed in one to two hours. The ammonia is expediently used in an excess of 10 to 30 mol % in order to ensure that the reaction material remains in the alkaline region. After the reaction is completed, the mixture is expediently further stirred at room temperature, then filtered off by suction from the ammonium chloride formed. The filtrate is worked up by distillation in a conventional manner. The process can also be carried out continuously. For certain fields of application, the resulting esters prepared according to the invention are so pure, even as crude products, that purification by distillation can be omitted.

EXAMPLE 1

300 g (1.28 mol) of 6-chloro-(6H)-dibenzo[c,e][1,2]-oxaphosphorine, dissolved in 346 ml of toluene, are added dropwise with stirring to a mixture of 76.5 g (1.663 mol) of absolute ethanol and 807 ml of toluene at $-15°$ to $-20°$ C. in the course of 1.5 hours. 23 g (1.35 mol) of ammonia are then introduced rapidly at this temperature. The mixture is further stirred and filtered off with suction and washed with toluene. The filtrate is concentrated by distillation at 12 mbar to an internal temperature of 75° C., finally at 1 mbar. 300 g of 6-ethoxy-(6H)-dibenzo[c,e][1,2]oxaphosphorine as solidified melt are obtained.

Solidification point: 45°–55° C. According to measurement by $^{31}P$—NMR, the product is approximately 95% pure. The yield is 96% of theory.

EXAMPLE 2

121.6 g (0.519 mol) of 6-chloro-(6H)-dibenzo[c,e][1,2]-oxaphosphorine, dissolved in 141 mol of toluene, are added dropwise with stirring to 350 g (7.6 mol) of absolute ethanol at $-15°$ C. and under a nitrogen atmosphere in the course of 90 minutes. 9 g (0.53 mol) of ammonia are then introduced rapidly at $-15°$ to $-10°$ C. with stirring. After the further stirring, the mixture is heated to 50° C., kept at this temperature for one hour and then filtered off with suction and washed with toluene. The filtrate is concentrated at 12 mbar to an internal temperature of 85° C., the residue is freed of amounts of salt at this temperature by filtration through a frit. The filtrate is distilled at 1.2 mbar. 110 g are obtained at an overhead temperature of 161°–163° C. This corresponds to a yield of 87% of theory.

I claim:

1. A process for preparing 6-alkoxy-(6H)-dibenzo[c,e][1,2]-oxaphosphorines of the formula (I)

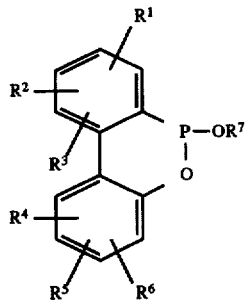

where $R^1$ to $R^6$ independently of one another are halogen, $(C_1-C_6)$alkyl or $(C_1-C_6)$alkoxy and $R^7$ is $(C_1-C_8)$alkyl, which comprises adding 6-halo-(6H)-dibenzo[c,e][1,2]-oxaphosphorines of the formula (II)

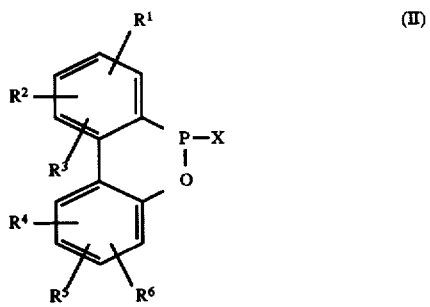

where $R^1$ to $R^6$ have the meaning specified above and X is halogen, to alcohols $R^7OH$, where $R^7$ has the meaning given above, at temperatures of −30° to +5° C. and then introducing ammonia at this temperature.

2. The process as claimed in claim 1, wherein at least one of the radicals $R^1$ to $R^3$ and $R^4$ to $R^6$ in each case are hydrogen and $R^7$ is $(C_1-C_4)$alkyl.

3. The process as claimed in claim 1, wherein $R^1$ to $R^6$ are hydrogen.

4. (Once Amended) The process as claimed in claim 1, wherein the alcohol $R^7OH$ is methanol, ethanol, isopropanol, butanol or octanol.

5. The process as claimed in claim 1, wherein the alcohol is used in excess to the compound of formula II.

6. The process as claimed in claim 1, further comprising an inert solvent.

7. The process as claimed in claim 1, wherein the compound of formula II is added to the alcohol at −30° C. to 0° C. under a nitrogen atmosphere.

8. The process as claimed in claim 1, wherein the ammonia is used in an excess of 10 to 30 mol %.

9. The process as claimed in, claim 1, wherein the addition time and reaction time with ammonia are each 1 to 2 hours.

10. The process as claimed in claim 2, wherein two of the radicals $R^1$ to $R^3$ and $R^4$ to $R^6$ in each case are hydrogen.

11. The process as claimed in claim 10, wherein the alcohol $R^7OH$ is ethanol.

12. The process as claimed in claim 4, wherein the amount of alcohol to chlorooxaphosphorine used is in a ratio of 1:1.1 to 1:20 mol.

13. The process as claimed in claim 12, wherein the amount of alcohol to chlorooxaphosphorine used is in a ratio of 1:1.15 to 1:15 mol.

14. The process according to claim 13, further comprising toluene or cyclohexane as an inert solvent.

15. The process according to claim 14, wherein chlorooxaphosphorine is added to the alcohol at −20° C. to −10° C. under a nitrogen atmosphere.

* * * * *